(12) United States Patent
Rodriguez Gutierrez et al.

(10) Patent No.: US 10,881,305 B2
(45) Date of Patent: Jan. 5, 2021

(54) WEARABLE THORACIC ELEMENT FOR DETECTING, MONITORING AND REPORTING THE PHYSIOLOGICAL STATUS OF AN INDIVIDUAL

(71) Applicant: Fundacio Eurecat, Barcelona (ES)

(72) Inventors: Rosa Rodriguez Gutierrez, Barcelona (ES); Daniel Blanco Sierra, Mataro (ES); Alberto Navarro Grueso, Madrid (ES); Juan Garcia Paredes, Rubi (ES)

(73) Assignee: Fundacio Eurecat, Barcelona (ES)

( * ) Notice: Subject to any disclaimer, the term of this patent is extended or adjusted under 35 U.S.C. 154(b) by 0 days.

(21) Appl. No.: 16/754,001

(22) PCT Filed: Oct. 2, 2018

(86) PCT No.: PCT/EP2018/076794
§ 371 (c)(1),
(2) Date: Apr. 6, 2020

(87) PCT Pub. No.: WO2019/068711
PCT Pub. Date: Apr. 11, 2019

(65) Prior Publication Data
US 2020/0345239 A1    Nov. 5, 2020

(30) Foreign Application Priority Data
Oct. 6, 2017 (EP) .................... 17382670

(51) Int. Cl.
*A61B 5/0205* (2006.01)
*A61B 5/00* (2006.01)
*A61B 5/0408* (2006.01)

(52) U.S. Cl.
CPC ........ *A61B 5/0205* (2013.01); *A61B 5/04087* (2013.01); *A61B 5/6804* (2013.01);
(Continued)

(58) Field of Classification Search
CPC ...... A61B 2562/0261; A61B 2562/043; A61B 2562/164; A61B 2562/227; A61B 5/0205;
(Continued)

(56) References Cited

U.S. PATENT DOCUMENTS

| 5,078,134 A | 1/1992 | Heilman et al. |
| 6,141,575 A | 10/2000 | Price |

(Continued)

FOREIGN PATENT DOCUMENTS

| CN | 203662728 | 6/2014 |
| EP | 1639939 | 3/2006 |

(Continued)

OTHER PUBLICATIONS

European Patent Office: PCT International Search Report dated Aug. 30, 2019; entire document.

*Primary Examiner* — Daniel L Cerioni
*Assistant Examiner* — Deirdre M Willgohs
(74) *Attorney, Agent, or Firm* — Allen, Dyer, Doppelt & Gilchrist, P.A.

(57) ABSTRACT

The thoracic element, in the shape of a band, comprises a support layer (5) including a first and second sensors (1),(2) and a processing unit (3) inside a casing (8). The first sensor (1) is a laminated strain gauge located on an elastic portion (5c) of the support layer (5) and the second sensor (2) is formed by a first and a second laminated electro-conductive elements (2a), (2b) cooperating to obtain an ECG measurement. Each of the sensors (1), (2) includes at their ends a connector (21a, 21b, 11a, 11b) to be attached to terminals (4a), (4b) of the casing (8). The laminated electro-conductive elements are superimposed and separated by an electric insulating rigid laminar layer (6). The support layer has two
(Continued)

openings (5*a*) and (5*b*) at a given distance, through which the electro-conductive elements (2*a* and 2*b*) can contact the skin of the individual.

12 Claims, 2 Drawing Sheets

(52) U.S. Cl.
CPC .......... *A61B 5/6823* (2013.01); *A61B 5/6831* (2013.01); *A61B 2562/0261* (2013.01); *A61B 2562/043* (2013.01); *A61B 2562/164* (2013.01); *A61B 2562/227* (2013.01)

(58) Field of Classification Search
CPC . A61B 5/04087; A61B 5/6804; A61B 5/6823; A61B 5/6831
USPC ........................................................ 600/484
See application file for complete search history.

(56) References Cited

U.S. PATENT DOCUMENTS

| | | | |
|---|---|---|---|
| 2008/0091097 | A1 | 4/2008 | Linti et al. |
| 2014/0343391 | A1 | 11/2014 | Korkala et al. |
| 2016/0120433 | A1 | 5/2016 | Hughes et al. |

FOREIGN PATENT DOCUMENTS

| | | |
|---|---|---|
| JP | H11-262476 | 9/1999 |
| WO | WO2005032366 | 4/2005 |
| WO | WO2017075703 | 5/2017 |
| WO | WO2017095861 | 6/2017 |

WEARABLE THORACIC ELEMENT FOR DETECTING, MONITORING AND REPORTING THE PHYSIOLOGICAL STATUS OF AN INDIVIDUAL

CROSS-REFERENCE TO RELATED APPLICATIONS

This application is the & 371 National Stage of International Application No. PCT/EP2018/076794, filed on Oct. 2, 2018, which claims the benefit of European Application Serial No. 17382670.2, filed on Oct. 6, 2017, the contents of which applications are hereby incorporated by reference in their entirety.

TECHNICAL FIELD

The present invention relates to a wearable element, such as a wearable thoracic band for detecting, monitoring and reporting the physiological status of an individual by incorporating different sensors. The present device, in the form of a wearable thoracic band, hereby disclosed is destined, but not limited, to the monitoring of an individual's physiological parameters in an exercising environment. However it may also be used in order to monitor the physiological parameters of an individual from a medical point of view on a daily basis.

STATE OF THE ART

Many devices and systems, specifically related to wearable bands for the monitoring of physiological parameters relative to an individual, are known in the current state of the art and they are applicable to many fields: such as exercising or sport environments and medical or safety applications.

Document WO2005032366 discloses a device wherein sensors that detect predetermined physiological parameters such as: heart rate, respiratory rate, fluid balance in the body, among many other parameters have been coated or integrated onto a textile material of an outfit or accessory worn straight on the skin, such as a sensor band.

Furthermore, it states that the electro-conductive surfaces have been designed flexible such that the conductivity may not be weakened whilst the surface of the electro-conductive element stretches.

However, said document, discloses a very generic device without defining how the sensors are arranged on the textile material or the disposition of the different sensors relative to each other.

Document EP1639939, discloses a system for detecting, monitoring and reporting human physiological data. The system includes a sensor device which generates data indicative of one or more physiological parameters of an individual wherein said sensor is placed in proximity to a portion of the individual's body. Said system also includes a processing unit which is connected to a central monitoring unit which processes the data gathered by the sensor or sensors.

CN203662728U discloses a chest strap for detecting physiological parameters including one pair of EGG electrodes and an elastic portion with a breathing sensor. However, said document falls to disclose how the sensors are positioned on the wearable device and what kind of wearable device is used and how the different elements are arranged.

Document WO2017075703, discloses a bio-sensing garment apparatus and method for applying electrodes to a fabric substrate. The bio-sensing garments disclosed can be functional for a variety of applications, such as electrocardiography (ECG), electromyography (EMG) or Respiratory Inductance Plethysmography (RIP) among others.

The conductors and electrodes may be integrated into any kind of garment or textile fabric which can then be integrated into a garment or used independently.

Furthermore, some of the embodiments disclosed include scalable metal-based or carbon-based electrode systems to overcome disadvantages associated with textile-based electrodes.

Furthermore, FIG. 8B of document WO2017075703, discloses a completed chest-band elastic, which can be either attached or integral to any one the biosensing garments described in this application. The chest-band elastic has integrated sensors such as an elongate member (functioning as a strain gauge) and one or more electrode arrays (which constitute one or more ECG laminar elongated members). These sensors are connected, by means of conductive pathways, to an arrangement of electrical connectors which are either mechanically fastened to the biosensing garment or arranged in a connector region (casing). Thus, FIG. 8B illustrates the proposed layout, evidencing the required space needed to include the different sensors and their associated conductive pathways in order to function.

US patent application no. 2014/343,391 A1 discloses a heart activity sensor structure which comprises a support layer with at least two electrodes (electrically isolated from one another) arranged on one side of the support layer, next to one another, configured to be placed against the skin of the user, in order to obtain an ECG signal, wherein the electrodes are connected to connectors of an electronic module. The electrodes and the electronic module are arranged on opposite sides of the support layer. An insulation layer may be inserted between the support layer and the electrodes.

The present device aims to solve several problems of current wearable thoracic bands and other bio-sensing garments, known in the prior art, by simplifying the configuration and materials used according to a particular arrangement of the sensors, specifically through the use of a multi-layer configuration wherein certain overlapping layers have specific functions, the materials used for the different layers which form said wearable band allowing the band to have different properties and the positioning of the sensors located inside the wearable band operating without connecting lines or cables among them.

BRIEF DESCRIPTION OF THE INVENTION

A wearable thoracic element is disclosed for detecting, monitoring and reporting the physiological status of an individual in an exercising environment but, it is not limited exclusively to this application. The thoracic element may also be used in order to monitor the status of an individual from a medical perspective such as the monitoring of elderly individuals or individuals with certain pathologies on a daily basis. It is known in the state of the art that said thoracic elements such as bands may comprise:

A first sensor aimed to collect data regarding a physiological parameter of the individual wearing said thoracic band, used for determining the respiratory rate of the individual;

a second sensor which collects data with regards to another physiological parameter of the individual wearing said thoracic band, for example used for determining the heart rate of the individual;

a processing unit, situated inside a casing of small dimensions, to which both the first sensor and the second sensor are connected to process data from said sensors; and terminals for the first sensor and terminals for the second sensor, wherein said terminals are positioned in said casing to which the connectors of each sensor are connected in order for the processing unit to receive the data of the different physiological parameters being monitored.

The wearable thoracic element of this invention in the form of a band is characterised in that it is formed by at least a primary layer.

The primary layer is a support layer that has two openings through which two electro-conductive laminated elements of one of the sensors are exposed resulting in the exposed portions of said electro-conductive elements acting as pads which can then be directly placed in contact with the individual in order to detect a physiological parameter. The support layer also includes an elastic portion onto which another sensor is placed which detects a second physiological parameter.

Both sensors are positioned adjacent to one another and on the same side of the band facing the user's body, of the support layer wherein the connectors of both sensors are in proximity to one another.

The casing containing the processing unit, which monitors and reports the data regarding the different parameters, is situated on the exterior side of a secondary layer, wherein said secondary layer acts as a covering layer.

In a preferred embodiment of this invention, a multi-layer configuration is used which may include a plurality of other layers such as: an electric insulating rigid laminar layer and a covering layer wherein said covering layer may act as an embellishment as well as a cover for the different sensors placed on the support band.

This multi-layer configuration and the positioning of the sensors inside of the thoracic band, substantially reduces the amount of cables or connections required.

The materials used for the different layers of the thoracic band may be either elastic, rigid, or in some cases the layers may be made up of several portions of different materials with different properties allowing any of the three layers to have both rigid and elastic portions according to the disposition of the different sensors.

In the case of the support layer, as it has previously been stated, it may be formed by a rigid or semi-rigid portion and an elastic portion which allows said portion to extend and adapt according to the individuals size and breathing.

The openings of the support layer, relative to the positioning of the second sensor, are located on the rigid portion of the support layer, which can be rigidized by placing an electric insulating rigid laminar layer in between the first and second electroconductive elements that form said second sensor, whereas the first sensor is positioned on the elastic portion of the support layer. In a preferred embodiment, the support layer is elastic throughout all its extension.

In a preferred embodiment, the materials used for the support and the covering layers of the thoracic band are elastic throughout all their extension wherein the covering layer covers the whole extension of the support layer and wherein said covering layer is an embellishment. As an example the material used for the support layer is a polyester fibre (PES), the material used for the covering layer is an elastomeric polyamide and the material used for the electric insulating rigid laminar layer is a thermo-adhesive PVC which has electric insulating properties.

The casing, containing the processing unit is situated on the external side of the covering layer of the thoracic band with the terminals facing their respective connectors from both the first and second sensor respectively placed on the support layer.

In a preferred embodiment of the wearable thoracic band, the connectors and their respective terminals are snap connectors. However, the mechanism used to join the connectors of both sensors to their respective terminals connected to the processing unit may be any other kind of quick connect terminal known in the state of the art.

Furthermore, the wearable thoracic band is also characterised in that, the first sensor is a laminated strain gauge, located on an elastic portion of the support layer.

In an embodiment of the invention, said laminated strain gauge is made up of two parallel extended linear strips with a connector placed on connecting tabs at the end of each strip, wherein one of the strips is longer than the other and both strips are joined together at one end distal from said connectors and said linear strips are part of a single entity.

When the individual wearing the thoracic band breathes, the strain gauge expands and contracts which results in a variation of the resistivity of the sensor thus allowing the processing unit to monitor and report the breathing rate variations of the individual through the detection of the sensors resistivity variations.

The second sensor is formed by a first laminated electro-conductive element and a second laminated electro-conductive element each of them provided with connectors situated on connecting tabs at two adjacent ends. Said laminated electroconductive elements cooperate in performing an ECG measurement.

This second sensor is placed in a part of the support layer which must be positioned on a central part of the individual's chest area, wherein the support layer comprises a first opening and a second opening at a given distance, through which a portion of said electro-conductive elements are exposed so they are able to be in contact, functioning as pads, directly with the skin of the individual on the interior side of the support layer.

For the wearable thoracic band to function adequately, it must be worn in such a way that the two openings of the support layer are placed perpendicular to the mid-sagittal plane of the Individual's body and the thoracic band must be placed approximately over the sternum with both openings positioned equidistantly from the sternum.

Therefore, the openings are located at both sides of a part of the support layer intended to be placed over a central part of the individual, so that the electro-conductive elements of the second sensor are located at both sides of said central part.

Once the thoracic band has been positioned in an optimal position, the two ECG laminated electro-conductive elements detect the individual's heart rate by determining the potential difference between the two electro-conductive elements.

The first and second ECG electro-conductive elements are superimposed but separated by an electric insulating rigid laminar layer, in order to avoid any errors when the sensor is detecting the heart rate by determining the potential difference between both electro-conductive elements.

Both the first and second laminated sensors are covered, at least, by a portion of the covering layer.

In a preferred embodiment, the first and second sensors are made up of a thermoplastic polyurethane (TPU) material.

The wearable thoracic band, which integrates the first sensor (which monitors the respiratory rate of the individual)

and the second sensor (which monitors the heart rate of the individual) is not limited exclusively to the use of these two sensors or the monitoring of the stated physiological parameters (respiratory and heart rate). The wearable thoracic band may include additional sensors which monitor other physiological parameters of the user or of his surroundings which are applicable to medical or exercising environments or the two mentioned sensors may detect and monitor different physiological parameters as the ones stated previously.

The connectors of both sensors are located in proximity and connected to terminals of the casing containing the processing unit, placed on the external side of the support layer.

It will be understood that references to geometric position, such as parallel, perpendicular, tangent, etc. allow deviations up to ±5° from the theoretical position defined by this nomenclature.

It will also be understood that any range of values given may not be optimal in extreme values and may require adaptations of the invention to these extreme values are applicable, such adaptations being within reach of a skilled person.

Other features of the invention appear from the following detailed description of an embodiment.

BRIEF DESCRIPTION OF THE FIGURES

The foregoing and other advantages and features will be more fully understood from the following detailed description of an embodiment with reference to the accompanying drawings, to be taken in an illustrative and not limitative, in which.

DETAILED DESCRIPTION OF AN EMBODIMENT

Figure 1:
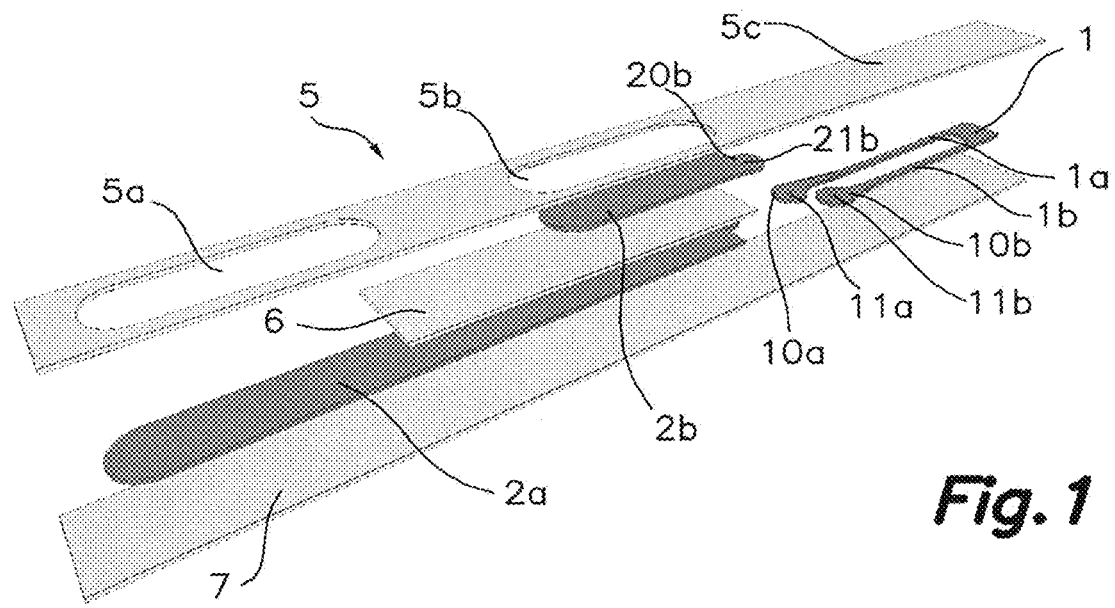
FIG. 1 illustrates a perspective view of the different elements that comprise the wearable thoracic band excluding the casing which includes the processing unit.

The foregoing and other advantages and features will be more fully understood from the following detailed description of an embodiment with reference to the accompanying drawings, to be taken in an illustrative and not limitative, in which:

FIG. 1 illustrates a perspective view, of one possible embodiment, of the different elements that comprise the wearable thoracic element in the form of a band although, the casing 8 containing the processing unit 3 and the terminals 4a and 4b, where the first sensor 1 and the second sensor 2 are connected, are not shown as they are positioned on the front side of the covering layer 7.

The first sensor 1, which is a laminated strain gauge, must be located on an elastic portion 5c of the support layer 5, if said support layer 5 is made up of several materials and not all of them are elastic and therefore there are different portions which comprise the support layer 5.

That is why, in order for the first sensor 1 to be able to expand and contract accordingly when the individual wearing the thoracic band inhales and exhales, allowing said first sensor 1 to detect the breathing rate of said individual, it must be located on an elastic portion 5c of the support layer.

According to a preferred embodiment, the support layer 5 is elastic throughout all its extension and the first sensor 1 of the wearable thoracic band is made up of two parallel extended strips 1a and 1b with a connector 11a and 11b placed on connecting tabs, 10a and 10b respectively, at the end of each strip, 1a and 1b respectively, wherein one of the strips 1a is longer than the other strip 1b and both stripe 1a, 1b are joined together at one end distal from said connectors 11a and 11b and said linear strips 1a, 1b are part of a single entity.

The second sensor 2 is formed by a first ECG laminated electro-conductive element 2a and a second ECG laminated electro-conductive element 2b each of them provided with connectors 21a and 21b situated on connecting tabs, 20a and 20b respectively, at two adjacent ends, wherein the first 2a and second 2b ECG electro-conductive elements are superimposed but separated by an electric insulating rigid laminar layer 6, and the support layer 5 comprising a first opening 5a and a second opening 5b at a given distance, through which a portion of said electro-conductive elements 2a and 2b are exposed so they are able to be in contact, as pads, directly with the skin of the individual on the interior side of the support layer 5.

In order to improve the contact between the pads formed by electro-conductive elements 2a and 2b of the second sensor 2 and the individual, the pads may include membranes which absorb the individuals' perspiration as well as specialised hydrogel membranes which also improve the electro-conductive elements 2a and 2b contact.

The materials used for both the first 1 and second 2 sensors must be electrically conductive and at least the first sensor 1 must have good elasticity properties.

The materials used for the different layers 5 and 7 of the thoracic band are elastic albeit, they are not required to have the same properties or be the same elastic material and therefore, the positioning of the first and second sensors, 1 and 2 respectively, is irrelevant as long as they are adjacent to each other and on the same side of the support layer 5.

According to one embodiment, the covering layer 7 only covers the laminated sensors 1 and 2 although, in a preferred embodiment, the covering layer 7 covers the whole extension of the support layer 5 wherein said covering layer 7 also acts as an embellishment for the thoracic band.

Figure 2:
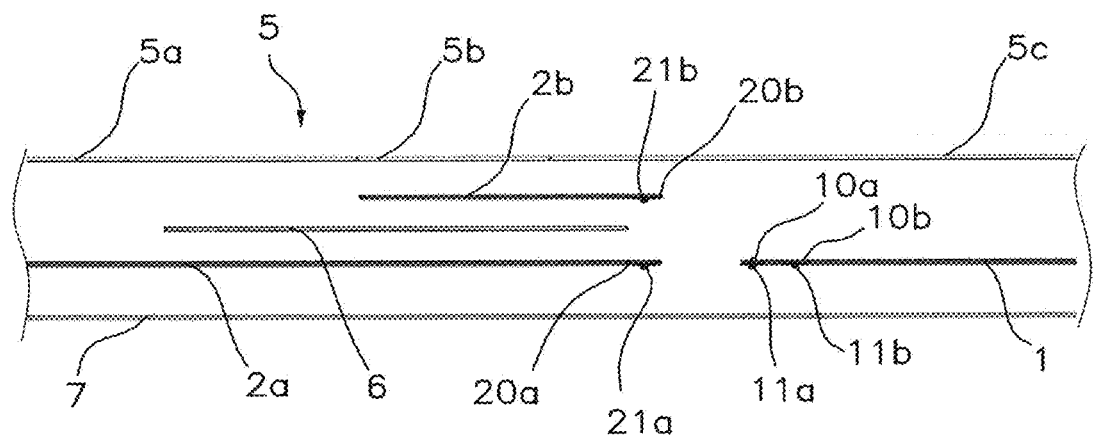
FIG. 2 illustrates a front view of the different elements that comprise the wearable thoracic band excluding the casing.

FIG. 2 illustrates a front view of the wearable thoracic band where we can clearly observe the placement of the sensors 1 and 2 and the different layers 5, 6 and 7 that comprise the thoracic band. The casing 8 which includes the processing unit 3 and the terminals 4a and 4b for the first 1 and second 2 sensor respectively is not represented in this figure in order to simplify it.

According to one embodiment, the first sensor 1 and the second sensor 2 are situated on the front side of the support layer 5, as the rear side is in direct contact with the individual, and they are covered by the covering layer 7 wherein said covering layer 7 may cover the whole extension of the support layer 5 or only those portions of the support layer (5) where the first and second sensors 1 and 2 are placed.

The first sensor 1 is a strain gauge and the second sensor 2 is formed by the first laminated ECG electro-conductive element 2a and the second laminated ECG electro-conductive element 2b.

The support layer 5 has two openings: the first opening 5a through which the first laminated ECG electro-conductive element 2a is exposed and the second opening 5b through which the second laminated ECG electro-conductive element 2b is exposed. The shape of the openings 5a and 5b may be any shape known in the state of the art which allows an adequate contact between the electro-conductive elements 2a and 2b and the individual. The opening of the support layer 5 may also be formed by a single opening instead of multiple openings, as shown in this particular embodiment of the thoracic band.

Placed in between the first and second laminated ECG electro-conductive elements 2a and 2b is the electric insulating rigid laminar layer 6.

The connectors 11a, 11b, 21a and 21b are placed at the end of connecting tabs 10a, 10b, 20a and 20b of both sensors 1 and 2 respectively located in proximity to each other with the connectors facing the terminals 4a and 4b located on the covering layer 7 relative to the position of the casing 8.

Figure 3:
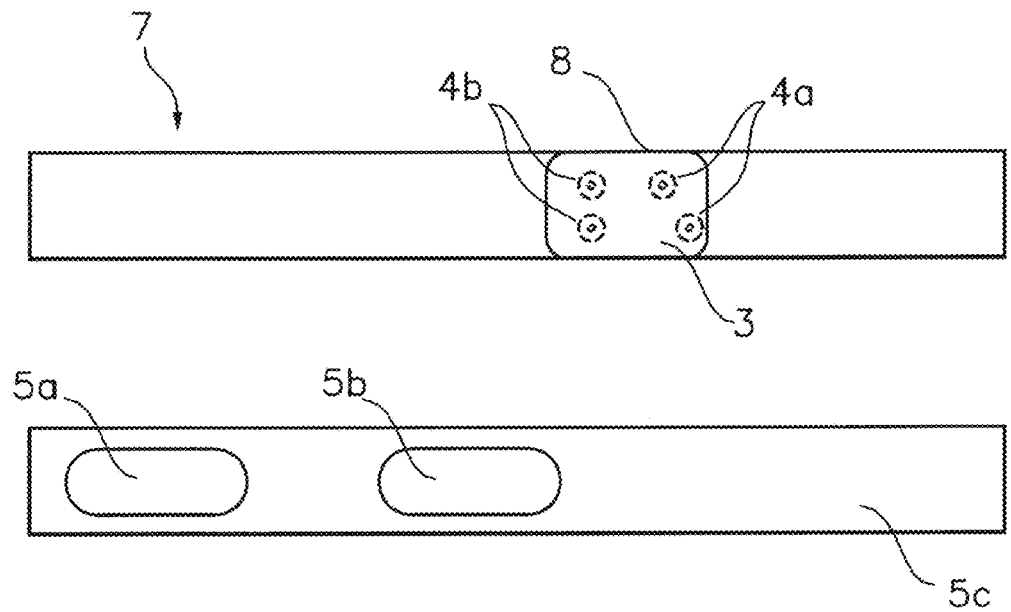
FIG. 3 illustrates a detailed view of the front of the covering layer and the rear side of the support layer.

FIG. 3 illustrates a detailed view of the front of the covering layer 7 and the rear side of the support layer 5 in a preferred embodiment of the wearable thoracic band.

The front view of the covering layer (7) shows the disposition of the casing 8 wherein said casing 8 contains the processing unit 3 and is situated on the external (or front) side of the covering layer 7 of the thoracic band.

In a preferred embodiment, the casing 8 contains two terminals 4a for the first sensor 1 and its respective connectors 11a and 11b and two terminals 4b for the second sensor 2 and its respective connectors 21a and 21b wherein, the terminals 4a and 4b are located in proximity to each other.

The casing (8) should cover said terminals 4a and 4b of both the first 1 and second sensor 2, respectively, but the terminals 4a and 4b have been represented in order to visualize how they are positioned.

The rear view of the support layer 5, allows us to see the disposition of the first opening 5a relative to the first electro-conductive element 2a and the disposition of the second opening 5b relative to the second electro-conductive element 2b of the second sensor 2.

Figure 4:
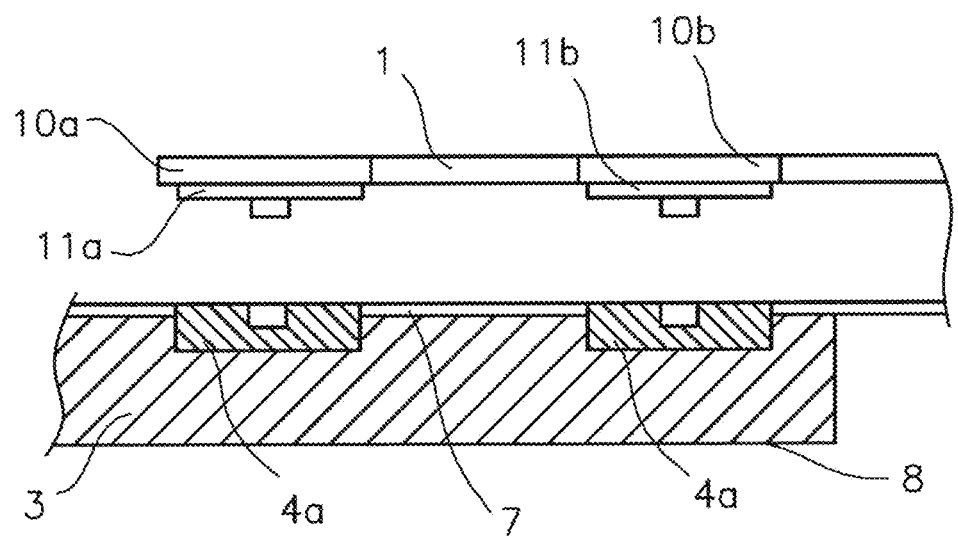
FIG. 4 illustrates a detailed view of the connection between the second sensors connectors and their respective terminals situated on the casing.

FIG. 4 illustrates an enlarged detailed view of the connection between the connectors 11a and 11b of the first sensor 1 and their respective terminals 4a situated on the casing 8. This detailed view of the connectors' arrangement between the first sensor 1 and the terminals 4a of the casing 8 is applicable to the connection of the second sensor 2 to the terminals 4b of the casing 8.

The first connector 11a placed on the connecting tab 10a relative to the extended strip 1a and the second connector 11b placed on the connecting tab 10b relative to the extended strip 1b are connected to the terminals 4a situated on the casing 8.

The two extended strips 1a and 1b are parallel and wherein the extended strip 1a is longer than the extended strip 1b corresponding to the first sensor 1 which is a laminated strain gauge.

In the case of the second sensor 2, the first connector 21a is situated on the connecting tab 20a relative to the first electro-conductive element 2a and the second connector 21b is situated on the connecting tab 20b relative to the second electro-conductive element (2b) which are connected to the terminals 4b situated on the casing 8 and wherein the terminals 4b are positioned on the same vertical axis.

The electric insulating rigid laminar layer 6 is placed in between the first and second electro-conductive elements 2a and 2b of the second sensor 2.

In a preferred embodiment of the wearable thoracic band, the connectors 11a, 11b, 21a and 21b and the terminals 4a and 4b are snap connectors.

It will be understood that various parts of one embodiment of the invention can be freely combined with parts described in other embodiments, even being said combination not explicitly described, provided there is no harm in such combination. Thus, the wearable thoracic element, in the form of a band previously disclosed, may be integrated into any kind of garment or textile fabric which can then be integrated into a garment or used independently.

The invention claimed is:

1. A wearable thoracic element configured to detect, monitor and report physiological parameters of an individual, said wearable thoracic element comprising:
   a first sensor comprising a laminated strain gauge and configured to determine a respiratory rate of the individual;
   a second sensor comprising at least one ECG laminated electro-conductive element and configured to determine a heart rate of the individual;
   a processing unit disposed inside of a casing, each one of said first sensor and said second sensor connected to said casing, said processing unit configured to process data from said first sensor and said second sensor; and
   each of said first sensor and said second sensor comprising a plurality of terminals, each one of said plurality of terminals of said first sensor and said second sensor is integrated within said casing;
   said first sensor and said second sensor covered by at least a portion of a covering layer; said laminated strain gauge having two parallel extended linear strips with connectors disposed on a first plurality of connecting tabs; said first plurality connecting tabs disposed at an end of each of said two parallel extended linear strips, one of said two parallel extended linear strips being longer than the other one of said two parallel extended linear strips, each of said two parallel extended linear strips being joined together at a distal end from said connectors forming a single entity, said single entity disposed on an elastic portion of at least one support layer, such that when the individual wearing the thoracic band breathes, said laminated strain gauge may expand and contract,
   said second sensor comprising a first ECG laminated electro-conductive element and a second ECG laminated electro-conductive element;
   each of said first ECG laminated electro-conductive element and said second ECG electro-conductive element being superimposed but separated by an electric insulating rigid laminar layer;
   each of said first ECG laminated electro-conductive element and said second ECG electro conductive element being provided with laterally offset connectors disposed on a second plurality of connecting tabs respectively, at two adjacent ends,
   said at least one support layer comprising a first opening and a second opening disposed at a predetermined longitudinal distance, through which a portion of each of said first ECG electro-conductive elements and said second ECG laminated electro-conductive elements is exposed and disposed in contact with the skin of the individual on an interior side of said at least one support layer; and
   said connectors of said strain gauge and said connectors of said second sensor adjacently disposed to one another.

2. The wearable thoracic element according to claim 1 wherein said connectors of said first sensor and said connectors of said second sensor are each connected to respective ones of said plurality of terminals integrated within said casing.

3. The wearable thoracic element according to claim 2 wherein said casing containing said processing unit is disposed on an external side of said covering layer with each one of said plurality of terminals facing respective ones of said connectors.

4. The wearable thoracic element according to claim 2 wherein each one of said connectors and each one of said terminals are snap connectors.

5. The wearable thoracic element according to claim 1 wherein said at least one support layer comprises an elastic material throughout all of its extension.

6. The wearable thoracic element according to claim 5 wherein each of said at least one support layer and said covering layer comprise an elastic material throughout all of their extension.

7. The wearable thoracic element according to claim 6 wherein said at least one support layer comprises a polyester fibre (PES) material.

8. The wearable thoracic element according to claim 1 wherein said electric insulating laminar layer comprises a thermos-adhesive PVC material.

9. The wearable thoracic element according to claim 6 wherein-said covering layer comprises an elastomeric polyamide material.

10. The wearable thoracic element according to claim 9 wherein said covering layer covers an entire extension of said at least one support layer and wherein said covering layer comprises an embellishment component; said wearable thoracic element is provided with a band.

11. The wearable thoracic element according to claim 1 wherein each of said first sensor and said second sensor comprise a thermoplastic polyurethane (TPU) material.

12. The wearable thoracic element according to claim 11 wherein said first opening and said second opening are disposed at least on both sides of said at least one support layer; each of said first opening and said second opening configured to be disposed on a central part of the individual, so that each said first ECG electro-conductive element and said second ECG electro-conductive element are disposed on corresponding sides of the central part of the individual.

* * * * *